United States Patent [19]

Crounse et al.

[11] 3,998,825
[45] Dec. 21, 1976

[54] TRIAZINYL-BENZOFLUORANS

[75] Inventors: Nathan Norman Crounse, Cincinnati; Paul Joseph Schmidt, Sharonville, both of Ohio

[73] Assignee: Sterling Drug Inc., New York, N.Y.

[22] Filed: July 31, 1975

[21] Appl. No.: 600,719

[52] U.S. Cl. .................. 260/249.5; 260/249.6; 260/249.8; 282/27.5
[51] Int. Cl.$^2$ ............ C07D 251/44; C07D 251/50; C07D 251/70
[58] Field of Search .......... 260/249.5, 249.6, 249.8

[56] References Cited
UNITED STATES PATENTS

| | | | |
|---|---|---|---|
| 3,183,231 | 5/1965 | Buell | 260/249.6 X |
| 3,867,383 | 2/1975 | Winter | 260/249.6 |

*Primary Examiner*—John M. Ford
*Attorney, Agent, or Firm*—Lynn T. Fletcher; B. Woodrow Wyatt

[57] ABSTRACT

Fluorans useful as color precursors, particularly in the art of carbonless duplicating are normally colorless and are represented by the structural formula

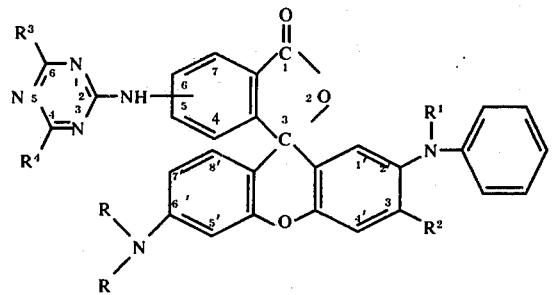

wherein R represents non-tertiary alkyl of one to four carbon atoms; $R^1$ and $R^2$ represent hydrogen or non-tertiary alkyl of one to four carbon atoms; $R^3$ and $R^4$ represent chlorine, or one of the groups —$NR^5$-(lower-alkylene)-$N(R^6)(R^7)$ or —$NR^5$-(lower-alkylene-$N^+(R^8)(R^9)(R^{10})$ An$^-$, in which $R^5$, $R^6$ and $R^7$ represent hydrogen or non-tertiary alkyl of one to four carbon atoms; $R^8$ and $R^9$ represent non-tertiary alkyl of one to four carbon atoms, $R^{10}$ represents non-tertiary alkyl of one to four carbon atoms, benzyl or benzyl substituted in the benzene ring by one or two of halo or alkyl of one to three carbon atoms; and An represents an anion.

11 Claims, No Drawings

# TRIAZINYL-BENZOFLUORANS

BACKGROUND OF THE INVENTION

1. Field of the Invention

This invention relates to 5/6-(4,6-disubstituted-s-triazin-2-yl)amino-2'-NR$^1$(C$_6$H$_5$)-3'-R$^2$-6'-dialkylaminofluorans useful as color precursors, particularly in the art of carbonless duplicating systems as, for example, pressure sensitive and thermal systems and to processes for preparing said 5/6-triazinyl-amino substituted-2'-anilino-6'-dialkylaminofluorans.

2. Description of the Prior Art

Several classes of organic cmpounds of widely diverse structural types are known to be useful as colorless precursors for carbonless duplicating systems. Among the more important classes, there may be named phenothiazines, for example, benzoyl leuco methylene blue; phthalides, for example, crystal violet lactone; fluorans, for example, 2'-anilino-6'-diethylaminofluoran and 2'-dibenzylamino-6'-diethylaminofluoran; and various other types of colorless precursors currently employed in commercially accepted carbonless copy systems. Moriga and Oda (Univ. Kyoto, Japan) in Kogyo Kagaku Zasshi 67 (7), 1054–8 (1964) [Chemical Abstracts 62: 2852a (1965)] describe the preparation and properties of a 3,3-bis(4-dimethylaminophenyl)phthalide which is substituted in the benzene ring of the phthalide moiety by a 4,6-dichloro-s-triazin-2-ylamino group. The compound is described as producing a green image when developed on bentonite in a simulated carbonless duplicating application. However, this prior art compound exhibits a number of deficiencies when employed in such a system which render it generally unsuitable for application in commercially feasible copy systems in light of the industry's standards for colorless precursors. Thus, its rate of color formation, upon contact with an electron withdrawing media such as an acidic clay or phenolic resin has been found to be rather slow. The intensity or tinctorial strength of the developed color produced by the reference compound has been found to be less than that generally found economically acceptable in the art when used within the concentrations usually employed in carbonless copy systems. Further, the solubility of the prior art compound in solvents regularly used in the copy system art for dissolving the dyes for microencapsulation is below that generally required to provide sufficient concentration of the dye to obtain satisfactory tinctorial strength in the developed form. Possibly the most important deficiency of the phthalide of Moriga and Oda is the low susceptibility to copiability of their color-developed form in standard copying machines, for example, a Xerox copier. By contrast, the compounds of this invention have been found to overcome the deficiencies of the prior art compound in that they proved to have a rapid rate of color formation on contact with acidic developing media; they have a good to excellent tinctorial strength to weight ratio; they are satisfactorily soluble in the usual microencapsulating solvents; and their developed color form is highly copiable in duplicating machines.

SUMMARY OF THE INVENTION

In one of its composition of matter aspects, the invention relates to certain 5/6-(4-R$^3$-6-R$^4$-s-triazin-2-yl)NH-2'-NR$^1$(C$_6$H$_5$)-3'-R$^2$-6'-N(R)$_2$fluorans which are final products useful as colorless precursors in carbonless duplicating systems.

In a second composition of matter aspect, the invention relates to certain 5/6-(4,6-dichloro-s-triazin-2-yl)NH-2'-N(R$^1$)-(C$_6$H$_5$)-3'-R$^2$-6'-N(R)$_2$fluorans which, in addition to having the same utility as the final products, are useful as intermediates for the preparation of other final products of the invention.

In one of its process aspects, the invention relates to a process for preparing the 5/6-(4,6-dichloro-s-triazin-2-yl)-NH-2'-NR$^1$(C$_6$H$_5$)-3'-R$^2$-6'-N(R)$_2$fluorans which comprises interacting the appropriate 5/6-NH$_2$-2'-NR$^1$(C$_6$H$_5$)-3'-R$^2$-6'-N(R)$_2$fluorans with cyanuric chloride.

In a second of its process aspects, the invention relates to a process for preparing the 5/6-(4-R$^3$-6-R$^4$-s-triazin-2-yl)NH-2'-NR$^1$(C$_6$H$_5$)-3'-R$^2$-6'-N(R)$_2$fluorans wherein each of R$^3$ and R$^4$ is a substituted amino group which comprises interacting the appropriate 5/6-(4,6-dichloro-s-triazin-2-yl)NH-2'-N(R$^1$)(C$_6$H$_5$)-3'-R$^2$-6'-N(R)$_2$fluoran with approximately two molecular proportions of the appropriate amine.

In a third of its process aspects, the invention relates to a process for the preparation of a quaternary ammonium salt of a 5/6-(4-R$^3$-6-R$^4$-s-triazin-2-yl)NH-2'-NR$^1$(C$_6$H$_5$)-3'-R$^2$-6'-N(R)$_2$fluoran in which one or both of R$^3$ and R$^4$ are substituted amino groups having within the substituting group a quaternizable nitrogen atom which comprises interacting the appropriate said basic amino compound with an appropriate quaternizing agent, for example, benzyl chloride.

DETAILED DESCRIPTION INCLUSIVE OF THE PREFERRED EMBODIMENTS

More specifically, this invention, in its composition of matter aspect, resides in the novel 5/6-(4-R$^3$-6-R$^4$-s-triazin-2-yl)NH-2'-NR$^1$(C$_6$H$_5$)-3'-R$^2$-6'-N(R)$_2$fluorans, which are useful as colorless precursors in the art of carbonless duplicating, and which are represented by the structural formula

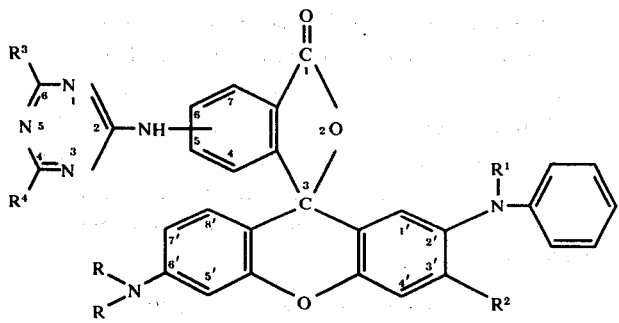

Formula I where R represents non-tertiary alkyl of one to four carbon atoms; $R^1$ and $R^2$ represent hydrogen or non-tertiary alkyl of one to four carbon atoms; $R^3$ and $R^4$ represent chlorine or one of the groups

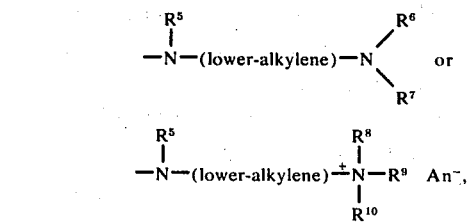

in which $R^5$, $R^6$ and $R^7$ represent hydrogen or non-tertiary alkyl of one to four carbon atoms; $R^8$ and $R^9$ represent non-tertiary alkyl of one to four carbon atoms; $R^{10}$ represents non-tertiary alkyl of one to four carbon atoms, benzyl or benzyl substituted in the benzene ring by one or two of halo or alkyl of one to three carbon atoms; and An represents an anion.

Even more specifically, this invention in its composition of matter aspect, resides in the 5-(4-$R^3$-6-$R^4$-s-triazin-2-yl)NH-2'-NR$^1$)C$_6$H$_5$)-3'-$R^2$-6'-N(R)$_2$fluorans having the structural formula

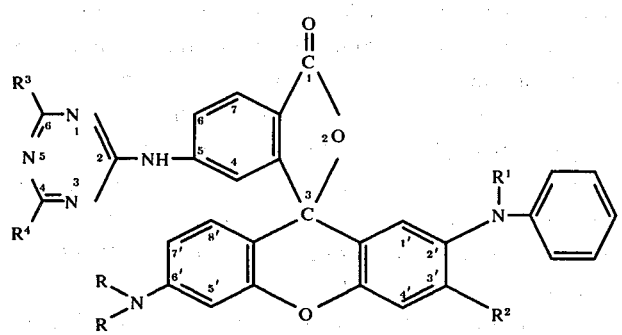

Formula II and in the 6-(4-$R^3$-6-$R^4$-s-triazin-2-yl)NH-2'-NR$^1$(C$_6$H$_5$)-3'-$R^2$-6'-N(R)$_2$fluorans having the structural formula

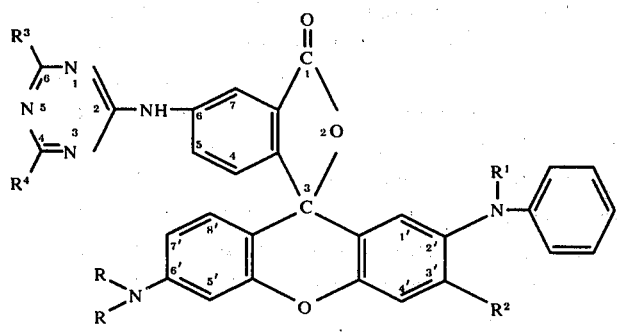

Formula III wherein in each formula, R, $R^1$, $R^2$, $R^3$ and $R^4$ have the same respective meanings indicated in relation to Formula I.

In the first particular embodiment in accordance with its composition of matter aspect, the invention sought to be patented resides in the novel 5/6-(4,6-dichloro-s-triazin-2-yl)-NH-2'-NR$^1$(C$_6$H$_5$)-3'-$R^3$-6'-N(R)$_2$fluorans of Formulas I, II and III wherein $R^3$ and $R^4$ are each chlorine and R, $R^1$ and $R^2$ each have the same respective meanings indicated in relation to Formulas I, II and III.

In a second particular embodiment in accordance with its composition of matter aspect, the invention sought to be patented resides in the novel 5/6-(4-$R^3$-6-$R^4$-s-triazin-2-yl)-NH-2'-NR$^1$(C$_6$H$_5$)-3'-$R^2$-6'-N(R)$_2$fluorans of Formulas I, II and III where $R^3$ and $R^4$ are each —NR$^5$-(lower-alkylene)-N(R$^6$)(R$^7$) and R, $R^1$, $R^2$, $R^5$, $R^6$ and $R^7$ each have the same respective meanings indicated in relation to Formulas I, II and III.

In a third particular embodiment in accordance with its composition of matter aspect, the invention sought to be patented resides in the novel 5/6-(4-R$^3$-6-R$^4$-s-triazin-2-yl)-NH-2'-NR$^1$(C$_6$H$_5$)-3'-R$^2$-6'-N(R)$_2$fluorans of Formulas I, II and III, in which R$^3$ is —NR$^5$-(lower-alkylene-N(R$^6$)(R$^7$) and R$^4$ is —NR$^5$-(lower-alkylene-N$^+$(R$^8$)(R$^9$)(R$^{10}$) An$^-$ and R, R$^1$, R$^2$, R$^5$, R$^6$, R$^7$, R$^8$, R$^9$, R$^{10}$ and An each have the same respective meanings given in relation for Formulas I, II and III.

In one of its process aspects, the invention sought to be patented resides in the process for the preparation of the novel 5/6-s-triazin-2-ylamino-6'-dialkylaminofluorans represented by Formulas I, II and III in which R$^3$ and R$^4$ are each chlorine which comprises interacting an appropriate 5/6-amino-2'-NHR$^1$(C$_6$H$_5$)-3'-R$^2$-6'-N(R)$_2$fluoran with approximately one molecular proportion of cyanuric chloride wherein R, R$^1$ and R$^2$ each have the same respective meanings given in relation to Formulas I, II and III.

In a second process aspect, the invention sought to be patented resides in the process for the preparation of the novel 5/6-s-triazin-2-ylamino-6'-dialkylaminofluorans represented by Formulas I, II and III in which R$^3$ and R$^4$ are each —NR$^5$-(lower-alkylene)-N(R$^6$)(R$^7$) which comprises interacting an appropriate 5/6-(4,6-dichloro-s-triazin-2-yl)NH-2'-NR$^1$(C$_6$H$_5$)-3'-R$^2$-6'-N(R)$_2$fluoran with approximately two molecular proportions of a compound having the formula

wherein R, R$^1$, R$^2$, R$^5$, R$^6$ and R$^7$ each have the same respective meanings indicated in Formulas I, II and III.

In a third process aspect, the invention sought to be patented resides in the process for the preparation of the novel 5/6-s-triazin-2-ylamino-6'-dialkylaminofluorans represented by Formulas I, II and III in which R$^3$ is —NR$^5$-(lower-alkylene)-N(R$^6$)(R$^7$) and R$^4$ is —NR$^5$-(lower-alkylene)-N$^+$(R$^8$)(R$^9$)(R$^{10}$) An$^-$ which comprises interacting a compound represented by Formulas I, II and III in which R$^3$ and R$^4$ are each —NR$^5$-(lower-alkylene)-N(R$^6$)(R$^7$) in which R$^6$ and R$^7$ are each non-tertiary alkyl of one to four carbon atoms with either an alkyl halide, a benzyl halide or a benzyl halide substituted in the benzene ring by one or two of halo or alkyl of one to three carbon atoms and wherein R, R$^1$, R$^2$, R$^5$, R$^8$, R$^9$, R$^{10}$ and An each have the same respective meanings given in Formulas I, II and III.

As used herein, the term "halo" includes bromo, chloro, fluoro and iodo. Similarly, the term "halide" includes bromide, chloride, fluoride and iodide.

As used herein, the term "non-tertiary alkyl" means saturated, aliphatic hydrocarbon groups, either straight or branched-chain, containing from one to four carbon atoms, and includes methyl, ethyl, propyl, isopropyl, butyl and isobutyl.

As used throughout, the term "(lower-alkylene)" means a divalent saturated straight or branched-chain aliphatic radical of from two to five carbon atoms having valence bonds attached to different carbon atoms. Thus, radicals represented by the term (lower-alkylene) are, for example, —CH$_2$CH$_2$—, —CH$_2$CH$_2$CH$_2$—, —(CH$_2$)$_4$—, —(CH$_2$)$_5$—, —CH(CH$_3$)CH$_2$—, —CH$_2$—CH$_2$—CH(CH$_3$)—CH$_2$—, —CH$_2$—CH(C$_2$H$_5$)—CH$_2$—, and the like.

As used herein, the term "An" represents Anion. By Anion is meant any monovalent ion derived from an organic or inorganic acid, H Anion, by removal of an acidic hydrogen ion. Exemplary anions are, halide, hydroxy, alkanoate, nitrate, phosphate, alkylsulfate and arylsulfate. Other monovalent anions are found in the literature, for example, Hackh's Chemical Dictionary, 3rd Edition (1946) at pages 12–13, and Chemical Abstracts Vol. 56, Nomenclature, at pages 72n–80n, both incorporated herein by specific reference thereto. As is known, one anion can be changed to another anion by use of conventional ion exchange methods. The halides, i.e., chloride, bromide, fluoride and iodide and in particular chloride and bromide are particularly preferred as the anions for the colorless precursors of this invention because of the generally ready availability of the quaternizing agents containing them. However, the scope of the compounds herein described and claimed is in no way to be thereto restricted.

The novel compounds represented by Formula I, Formula II and Formula III above are essentially colorless in the depicted lactone form. When contacted with an acidic medium, for example, silica gel, or one of the types regularly employed in carbonless duplicating systems, for example, silton clay or phenolic resins, they readily develop a colored image of good to excellent tinctorial strength. Moreover, it has been found that when the compounds of Formula I, Formula II and Formula III are intimately mixed with an acidic developer of the type generally employed in thermal papers, that is papers which produce a colored image when contacted with a heated stylus or heated type, for example, bis-phenol A, heating of the mixture produces a black-green colored material. It has also been found that when the compounds of this invention are converted to a water-soluble form, the essentially colorless water-soluble compound is substantive to cellulose, for example, paper.

The rapid development of color on contact of the compounds of Formula I, Formula II and Formula III with silica gel, silton clay or a phenolic resin demonstrates that they are highly suitable for use as colorless precursors in pressure-sensitive carbonless duplicating systems. Their ability to readily form a deep color when heated to admixture with an acidic developer such as bisphenol A, makes them useful in thermal paper marking systems, either where an original or a duplicate copy is prepared by contacting the thermal paper with a heated stylus or heated type in any of the methods generally known in the art. The substantivity of cellulose of the water-soluble forms of the compounds of Formula I, Formula II and Formula III makes them effective for dyeing paper. The dyed paper then may be used for producing images as originals by contacting with an ink containing an acidic developing substance. Moreover, the dyed paper may be used in a pressure-sensitive system in which it is contacted with a matching sheet coated with microencapsulated acidic developing substance.

As stated above, the compounds of Formula I, Formula II and Formula III are useful as color precursors, particularly in the art of carbonless duplicating systems. As with other colorless precursors currently in use in the art, the compounds are colorless under neutral or basic conditions, but become colored when contacted with an acidic material such as silica gel, a phenolic resin or an acidic clay. It is frequently desired that the images produced by such color precursors be copiable by xerographic means. A widely used color precursor is 3,3-bis(4-dimethylaminophenyl)-6-dimethylaminophthalide or, as this compound has been more simply designated, crystal violet lactone. Crystal violet lactone produces a blue image which has the advantage of being intense but which suffers the disadvantage of being poorly copiable by xerographic means. To counteract this disadvantage, other color precursors have been mixed with crystal violet lactone as described, for example, in U.S. Pat. No. 3,525,630. The images produced by the compounds of Formulas I, II and II, although generally less intense in color than images produced by crystal violet lactone, are readily copiable by xerographic means. For this reason, the difficulties inherent in using mixed color precursors to achieve xerographic copiability can be avoided by using a compound of Formulas I, II and III alone.

The best mode contemplated by the inventors of carrying out this invention will now be described as to enable any person skilled in the art to which it pertains to make and use the same.

The compounds represented by Formulas I, II and III wherein $R^3$ and $R^4$ are each chlorine have dual utilities in that they are useful in the free-base form as final products of the invention having the same utility as colorless precursors and they are also intermediates both in the acid-addition salt form and in the free-base form to those final products of Formulas I, II and III wherein one or both of $R^3$ and $R^4$ represent a substituted amino moiety of the type depicted in relation to Formulas I, II and III. The compounds in which $R^3$ and $R^4$ are each chlorine are prepared by interacting the appropriate 5/6-amino-2'-$NR^1$-($C_6H_5$)-3'-$R^2$-6'-dialkylaminofluoran with approximately an equimolar quantity of cyanuric chloride. The reaction is advantageously carried out in a single or a mixed solvent system consisting of aprotic and/or protic solvents. When the hydrochloride salt form of the product is desired, the reaction is carried out in the absence of alkali. When the free-base form is required, sufficient aqueous sodium hydroxide solution to neutralize the hydrochloric acid generated during the reaction is added. Particularly preferred solvents for the formation of the hydrochloride salt form are toluene and acetone, and for the free-base form, a mixture of acetone and dioxane. The reaction is best carried out in an aprotic solvent system at a temperature in the range of 0° C to the reflux temperature of said solvent system in the absence of alkali, and in a protic solvent system at a temperature in the range of 0° to 5° C when aqueous alkali is employed. When obtained in the form of its hydrochloride salt, the 5/6-(4,6-dichloro-s-triazin-2-yl)amino-2'-$NR^1$($C_6H_5$)-3'-$R^2$-6'-dialkylaminofluoran is isolated by filtration followed by washing with an inert organic solvent, for example, toluene or diethyl ether and then dried. When the dichlorotriazinyl products are to be utilized as intermediates to other products represented by Formulas I, II or III, it is unnecessary to isolate the product and the slurry containing the intermediate in the form of the free-base may be used directly. Alternatively, the acid-addition salt form of the dichlorotriazinyl products may be converted in situ to the free-base form for interaction with the appropriate substituted amine required for the desired compound.

The 5/6-amino-2'-$NR^1$($C_6H_5$)-3'-$R^2$-6'-dialkylaminofluorans required for the preparation of the compounds of Formulas I, II and III in which $R^3$ and $R^4$ are each chlorine are known compounds. Cyanuric chloride is a known compound and is commercially available.

The compounds of Formulas I, II and III wherein one or both of $R^3$ and $R^4$ are —$NR^5$-(lower-alkylene)-$N(R^6)(R^7)$, are each prepared by essentially the same general procedure. Thus, the appropriate 5/6-(4,6-dichloro-s-triazin-2-yl)amino-2'-$NR^1$-($C_6H_5$)-3'-$R^2$-6'-dialkylaminofluoran is interacted with the appropriate dialkylaminoalkylamine. When it is desired to prepare a monosubstituted compound, approximately one molecular proportion of the "side chain" is employed and when it is desired to obtain a disubstituted compound, approximately two molecular proportions of the side chain is employed. The reaction is conveniently carried out in a solvent mixture consisting of aprotic and/or protic solvents, for example, a mixture of p-dioxane and acetone in the presence of sufficient alkali to absorb the hydrochloric acid generated at a temperature in the range of 60° to 90° C, preferably at the reflux temperature of the solvent mixture. Although the reaction can be run by dissolving the appropriate 5/6-(4,6-dichloro-s-triazin-2-yl)amino-2'-$NR^1$($C_6H_5$)-3'-$R^2$-6'-dialkylaminofluoran in the solvent system, it is generally satisfactory and preferred to use this intermediate as obtained in its own reaction mixture without prior isolation. The desired disubstituted triazinylfluoran is isolated from its reaction mixture by evaporating the solvent and triturating the residue with an inert organic solvent, for example, n-hexane.

The quaternary ammonium compounds of Formulas I, II and III, wherein one or both of $R^3$ and $R^4$ represent the group —$NR^5$-(lower-alkylene-$N^+(R^8)(R^9)(R^{10})$ $An^-$ are prepared by interacting an appropriate compound represented by Formulas I, II or III in which one or both of $R^3$ and $R^4$ are —$NR^5$-(lower-alkylene)-$N(R^6)(R^7)$ wherein $R^6$ and $R^7$ are each non-tertiary alkyl of one to four carbon atoms with an alkyl halide or a substituted or unsubstituted benzyl halide. The quaternization is conveniently carried out either with or without solvent. Suitable solvents are to be found among polar and non-polar solvents and mixtures of such solvents. Among these may be mentioned water; the lower-alkanols, for example, ethyl alcohol; aromatic hydrocarbons, for example, benzene and toluene; ketones, for example, acetone; and acylnitriles, for example, acetonitrile. The reaction is generally carried out in the temperature range of 50° to 100° C of the chosen solvent system. Illustrative of the alkyl halides useful for this conversion are, for example, methyl chloride, ethyl bromide and butyl bromide. Benzyl halides useful for the conversion are, for example, benzyl chloride, o-chlorobenzyl chloride, benzyl bromide, 2,5-dimethylbenzyl chloride, 4-bromobenzyl bromide, benzyl iodide, 3,4-dichlorobenzyl chloride, 3-fluorobenzyl chloride and the like.

The reactive amine intermediates required for interaction with the appropriate 5/6-(4,6-dichloro-s-triazin-2-yl)$NH$-2'-$NR^1$($C_6H_5$)-3'-$R^2$-6'-dialkylaminofluoran to obtain the compounds of Formulas I, II and III are known compounds whose preparation is well-known in the prior art. The following compounds are exemplary of these reactive amine compounds useful in the practice of this invention.

3-Dimethylaminopropylamine,
3-Diethylaminopropylamine,
2-Dimethylaminoethylamine,
4-Diethylaminobutylamine,
5-Diethylaminopentylamine,
2-Diisopropylaminoethylamine,
3-Dibutylaminopropylamine, Ethylenediamine,
2-Diethylaminoethylamine, and
4-Diethylamino-1-methyl-butylamine.

The molecular structures of the compounds of the invention were assigned on the basis of the modes of synthesis and study of their infrared, ultraviolet and NMR spectra.

The following examples will further illustrate the invention without, however, limiting it thereto. All melting points are uncorrected.

EXAMPLE 1

To a stirred solution of 0.48 g of 6-amino-2'-anilino-6'-diethylaminofluoran in 25 ml of acetone, there was added during a period of 10 minutes a solution of 0.18 g cyanuric chloride in 20 ml of acetone. When the addition was complete, the mixture was stirred for a period of approximately one-half hour at ambient temperature. The reaction mixture was then poured into an evaporating dish and the acetone evaporated to approximately half the original volume. The solid, which separated, was collected by filtration, washed first with toluene, and then with diethyl ether and dried to a constant weight in a vacuum oven at 50° C to obtain the product represented by Formula III in which R is —$C_2H_5$; $R^3$ and $R^4$ are each Cl; and $R^1$ and $R^2$ are each hydrogen in the form of its hydrochloride salt. This product, which was a green powder, remained unmelted up to 300° C. A solution of the product in 25 percent water and 75 percent acetone when spotted on silica gel, a phenolic resin or an acidic clay, develops a greenish-black color.

EXAMPLE 2

To a stirred solution of 0.48 g of 5-amino-2'-anilino-6'-diethylaminofluoran in 70 ml of toluene there was added during a period of one-half hour a solution of 0.18 g of cyanuric chloride in 10 ml of toluene. The resultant green solution was stirred at ambient temperature for a period of approximately 2 hours and then slowly heated to reflux during a period of approximately 2 hours. At reflux temperature, the color of the solution changed from green to blue. Upon cooling to room temperature, a green-black solid separated. The solid was collected by filtration and dried in vacuo at 60° C overnight to yield the product represented by Formula II where R is —$C_2H_5$; $R^3$ and $R^4$ are each Cl; and $R^1$ and $R^2$ are each hydrogen in the form of its hydrochloride salt. The product remained unmelted up to 290° C. A solution of the product in 25 percent water and 75 percent acetone spotted on silica gel, a phenolic resin or an acidic clay, develops a green-black color.

EXAMPLE 3

To a stirred slurry consisting of 12 ml of acetone and 0.48 g of 6-amino-2'-anilino-6'-diethylaminofluoran cooled to approximately 0° C by means of an ice/salt bath, there was simultaneously added a solution of 0.182 g of cyanuric chloride in 5 ml of acetone and 0.4 ml of 10 percent aqueous sodium hydroxide solution during a period of approximately 10 minutes whilst maintaining the internal temperature in the range of 0° to 5° C. The internal temperature rose briefly to 20° C after the addition but was rapidly recooled to 5° C prior to the addition of a solution of 0.10 g of 3-dimethylaminopropylamine in 2.5 ml of acetone. The reaction mixture was then warmed to 20° C and a volume of p-dioxane approximately that of the reaction mixture, a solution of 0.20 g of 3-dimethylaminopropylamine in 2.5 ml of acetone and 0.4 ml of 10 percent aqueous sodium hydroxide solution were added. The resultant solution was then heated at reflux for approximately 2 hours, cooled and the solvent removed by evaporation at reduced pressure. The oily product which remained was triturated with n-hexane to obtain a solid which was collected by filtration and washed with fresh n-hexane. Upon drying in vacuo to a constant weight, as a light green colored powder, 0.80 g of the product represented by Formula III in which R is —$C_2H_5$; $R^3$ and $R^4$ are each —NH—($CH_2CH_2CH_2$)—N($CH_3$)$_2$; and $R^1$ and $R^2$ are each hydrogen. An acetone solution of the product spotted on silica gel, a phenolic resin or an acidic clay develops a black color.

EXAMPLE 4

To a stirred slurry of 0.47 g of 5-amino-2'-anilino-6'-diethylaminofluoran, 50 ml of acetone and 50 ml of p-dioxane, there was simultaneously added a solution of 0.182 g of cyanuric chloride in 5 ml of acetone and 0.4 ml of 10 percent aqueous sodium hydroxide solution while maintaining the temperature range of 0° to 5° C by means of an ice/salt bath. The resultant solution was stirred for a period of approximately 1 hour while maintaining the temperature in the range of 0° to 5° C. There was added to the reaction mixture 0.31 g of 3-dimethylaminopropylamine and the mixture was gradually warmed to 20° C at which temperature a solid precipitated. The slurry was then heated at reflux for approximately 2 hours, cooled and set aside briefly. The supernatant liquid was decanted from the settled-out green-black tarlike solid and the solid collected by filtration. Upon drying at 50° C in vacuo, the tar-like solid gave way to a friable material. A solution of the solid which was the product of Formula II in which R is $C_2H_5$; $R^1$ and $R^2$ are each hydrogen; and $R^3$ and $R^4$ are each —NH—($CH_2CH_2CH_2$)—N($CH_3$)$_2$ in a mixture of water and ethanol was prepared. The solution was stirred while 0.13 g benzyl chloride was added and then heated at approximately 50° C for a period of 15 minutes, cooled, and the solvent evaporated. The green, tar-like product, represented by Formula II where R is —$C_2H_5$; $R^1$ and $R^2$ are each hydrogen; $R^3$ is —NH—($CH_2CH_2CH_2$)—N$^+$($CH_3$)$_2$($C_6H_5CH_2$); and $R^4$ is —NH—($CH_2CH_2CH_2$)—N($CH_3$)$_2$, when dissolved in water spotted on silica gel, a phenolic resin, or an acidic clay develops a black color.

EXAMPLE 5

The utility of the compounds described in the foregoing examples as color forming components in thermal copying systems was demonstrated as follows. A portion of the product of Example 4 (Formula II: R is $C_2H_5$; $R^1$ and $R^2$ are each hydrogen; $R^3$ is —NH—($CH_2CH_2CH_2$)—N$^+$($CH_3$)$_2$($C_6H_5CH_2$) Cl$^-$; and $R^4$ is —NH—($CH_2CH_2CH_2$)—N($CH_3$)$_2$ and an equal weight of bisphenol A were intimately mixed. A thin layer of the greenish-white-colored powder mixture was then spread on a white porcelain tile and heated to approximately 140° C at which temperature the mixture developed a black-green color.

| Example | R | R$^1$ | R$^2$ | R$^3$ | R$^4$ |
|---|---|---|---|---|---|
| 6 | C$_3$H$_7$ | H | C$_2$H$_5$ | NH(CH$_2$)$_4$N(C$_2$H$_5$)$_2$ | NH(CH$_2$)$_4$N(C$_2$H$_5$)$_2$ |
| 7 | C$_2$H$_5$ | CH$_3$ | H | NH(CH$_2$)$_5$N(C$_2$H$_5$)$_2$ | NH(CH$_2$)$_5$N(C$_2$H$_5$)$_2$ |
| 8 | C$_2$H$_5$ | H | CH$_3$ | Cl | NH(CH$_2$)$_3$N(CH$_3$)$_2$ |
| 9 | CH$_3$ | H | H | N(CH$_3$)(CH$_2$)$_3$N—(CH$_3$)$_2$ | N(CH$_3$)(CH$_2$)$_3$N—(CH$_3$)$_2$ |
| 10 | C$_3$H$_7$ | H | CH$_3$ | N(C$_4$H$_9$)(CH$_2$)$_2$N—(C$_2$H$_5$)$_2$ | N(C$_4$H$_9$)(CH$_2$)$_3$N—(C$_2$H$_5$)$_2$ |
| 11 | C$_2$H$_5$ | C$_2$H$_5$ | C$_4$H$_9$ | Cl | N(CH$_3$)(CH$_2$)$_2$N—(CH$_3$)$_2$ |
| 12 | CH$_3$ | C$_2$H$_5$ | CH$_3$ | NH(CH$_2$)$_2$N—(i-C$_3$H$_7$)$_2$ | NH(CH$_2$)$_2$N—(i-C$_3$H$_7$)$_2$ |
| 13 | C$_2$H$_5$ | H | H | NH(CH$_2$)$_3$N—(n-C$_4$H$_9$)$_2$ | NH(CH$_2$)$_3$N—(n-C$_4$H$_9$)$_2$ |
| 14 | C$_2$H$_5$ | C$_3$H$_7$ | H | NH(CH$_2$)$_2$NH$_2$ | NH(CH$_2$)$_2$NH$_2$ |
| 15 | C$_2$H$_5$ | H | sec-C$_4$H$_9$ | NH(CH$_2$)$_2$N(C$_2$H$_5$)$_2$ | NH(CH$_2$)$_2$N(C$_2$H$_5$)$_2$ |
| 16 | C$_3$H$_7$ | H | H | NH(CH$_2$)$_3$N$^+$(CH$_3$)$_2$—(C$_6$H$_5$CH$_2$) Br$^-$ | NH(CH$_2$)$_3$N$^+$(CH$_3$)$_2$—(C$_6$H$_5$CH$_2$) Br$^-$ |
| 17 | CH$_3$ | H | C$_3$H$_7$ | NH(CH$_2$)$_5$N(C$_2$H$_5$)$_2$ | NH(CH$_2$)$_5$N(C$_2$H$_5$)$_2$ |
| 18 | C$_2$H$_5$ | H | H | NHCH(CH$_3$)(CH$_2$)$_3$N—(C$_2$H$_5$)$_2$ | NHCH(CH$_3$)(CH$_2$)$_3$N—(C$_2$H$_5$)$_2$ |
| 19 | sec-C$_4$H$_9$ | CH$_3$ | H | NH(CH$_2$)$_2$N$^+$(CH$_3$)$_2$—(2-Cl-C$_6$H$_4$CH$_2$) Cl$^-$ | NH(CH$_2$)$_2$N(CH$_3$)$_2$ |
| 20 | C$_2$H$_5$ | H | n-C$_4$H$_9$ | NH(CH$_2$)$_3$N(C$_2$H$_5$)$_2$ | NH(CH$_2$)$_3$N$^+$(C$_2$H$_5$)$_2$—(2,5-(CH$_3$)$_2$—C$_6$H$_3$CH$_2$) Cl$^-$ |
| 21 | CH$_3$ | CH$_3$ | CH$_3$ | NH(CH$_2$)$_3$N(CH$_3$)$_2$ | NH(CH$_2$)$_3$N$^+$(CH$_3$)$_2$—(4-Br-C$_6$H$_4$CH$_2$) Br$^-$ |
| 22 | C$_3$H$_7$ | H | H | NH(CH$_2$)$_5$N(C$_2$H$_5$)$_2$ | NH(CH$_2$)$_5$N(C$_2$H$_5$)$_2$—(C$_6$H$_5$CH$_2$) I$^-$ |
| 23 | C$_2$H$_5$H | C$_2$H$_5$ | NH(CH$_2$)$_3$-N$^+$(CH$_3$)$_2$— | N(CH$_3$)$_3$N$^+$(CH$_3$)$_2$—(2-F-C$_6$H$_4$CH$_2$) Cl$^-$ | (2-F-C$_6$H$_4$CH$_2$) Cl$^-$ |
| 24 | CH$_3$ | n-C$_4$H$_9$ | H | NH(CH$_2$)$_2$N(C$_2$H$_5$)$_2$ | NH(CH$_2$)$_2$N$^+$(C$_2$H$_5$)$_2$—(3,4-Cl$_2$-C$_6$H$_3$CH$_2$) Cl$^-$ |
| 25 | C$_2$H$_5$ | H | C$_3$H$_7$ | NH(CH$_2$)$_3$N(CH$_3$)$_2$ | NH(CH$_2$)$_3$N$^+$(CH$_3$)$_2$—(3,4-(CH$_3$)$_2$—C$_6$H$_3$CH$_2$) Cl$^-$ |
| 26 | C$_2$H$_5$ | H | H | NH(CH$_2$)$_4$N(C$_2$H$_5$)$_2$ | NH(CH$_2$)$_4$N$^+$(C$_2$H$_5$)$_2$—(3-F-C$_6$H$_4$CH$_2$) Cl$^-$ |
| 27 | CH$_3$ | H | CH$_3$ | NH(CH$_2$)$_3$N(CH$_3$)$_2$ | NH(CH$_2$)$_3$N$^+$(CH$_3$)$_2$ (2,4-Cl$_2$.C$_6$H$_3$CH$_2$) Cl$^-$ |
| 28 | C$_2$H$_5$ | sec-C$_4$H$_9$ | H | NH(CH$_2$)$_3$N(C$_2$H$_5$)$_2$ | NH(CH$_2$)$_3$N$^+$(C$_2$H$_5$)$_2$—(3-Br-C$_6$H$_4$CH$_2$) Br$^-$ |
| 29 | n-C$_4$H$_9$ | H | CH$_3$ | NH(CH$_2$)$_2$N$^+$(CH$_3$)$_2$ (2-CH$_3$—C$_6$H$_4$CH$_2$) Cl$^-$ | NH(CH$_2$)$_2$N$^+$(CH$_3$)$_2$—(2-CH$_3$—C$_6$H$_4$CH$_2$) Cl$^-$ |
| 30 | CH$_3$ | H | C$_2$H$_5$ | NH(CH$_2$)$_2$N$^+$(C$_2$H$_5$)$_2$—(CH$_3$) Cl$^-$ | NH(CH$_2$)$_2$N$^+$(C$_2$H$_5$)$_2$ (CH$_3$) Cl$^-$ |
| 31 | C$_2$H$_5$ | C$_3$H$_7$ | H | NH(CH$_2$)$_3$N(C$_4$H$_9$) | NH(CH$_2$)$_3$N$^+$(C$_4$H$_9$)$_3$—Br$^-$ |
| 32 | C$_2$H$_5$ | H | CH$_3$ | NH(CH$_2$)$_5$N(C$_2$H$_5$)$_2$ | NH(CH$_2$)$_5$N$^+$(C$_2$H$_5$)$_3$ I$^-$ |
| 33 | CH$_3$ | H | CH$_3$ | NH(CH$_2$)$_2$N$^+$(CH$_3$)$_2$—(C$_3$H$_7$) Br$^-$ | NH(CH$_2$)$_2$N$^+$(CH$_3$)$_2$ (C$_3$H$_7$) Br$^-$ |

EXAMPLE 34

Hand sheets dyed with the compound of Example 4 above (Formula II: R is C$_2$H$_5$; R$^1$ and R$^2$ are each hydrogen; R$^3$ is —NH—(CH$_2$CH$_2$CH$_2$)-N$^+$(CH$_3$)$_2$(C$_6$H$_5$CH$_2$) Cl$^-$; and R$^4$ is —NH—(CH$_2$CH$_2$CH$_2$)—N(CH$_3$)$_2$ were prepared by adding a 0.5 percent aqueous solution of the compound to an aqueous slurry of a cellulosic pulp (bleached Kraft fiber). The dyestuff was exhausted onto the fiber and the sheets formed on a laboratory sheet mold. The sheet was pressed between blotting paper in a hydraulic press and then air dried. When the paper thus prepared was streaked with a toluene solution of a phenolic resin, a black-green colored image was formed.

We claim:
1. A compound having the formula

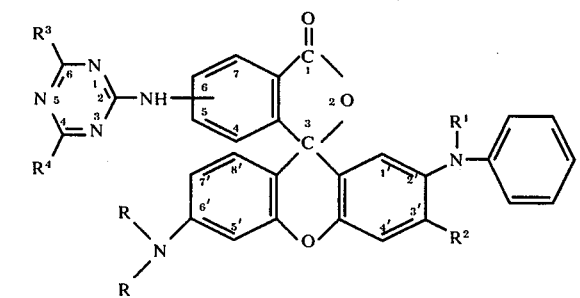

where R represents non-tertiary alkyl of one to four carbon atoms; R$^1$ and R$^2$ represent hydrogen or non-tertiary alkyl of one to four carbon atoms; R$^3$ and R$^4$ represent chlorine, or one of the groups

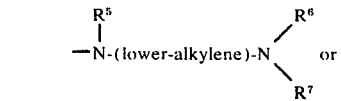

-continued

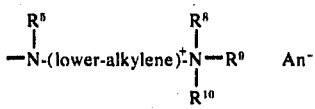

in which $R^5$, $R^6$ and $R^7$ represent hydrogen or non-tertiary alkyl of one to four carbon atoms; $R^8$ and $R^9$ represent non-tertiary alkyl of one to four carbon atoms; $R^{10}$ represents non-tertiary alkyl of one to four carbon atoms, benzyl or benzyl substituted in the benzene ring by one or two of halo or alkyl of one to three carbon atoms; and An represents an anion selected from the group consisting of halides, hydroxy, alkanoates, nitrate, phosphate, alkylsulfates and arylsulfates.

2. A compound according to claim 1 having the formula

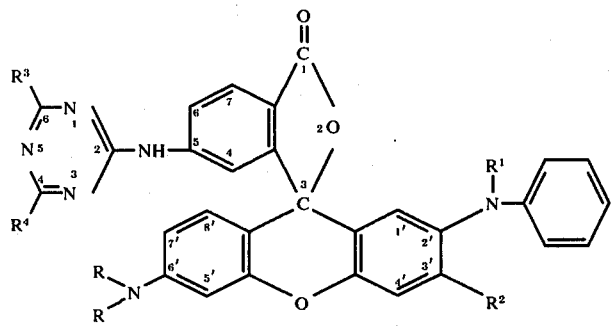

where R, $R^1$, $R^2$, $R^3$ and $R^4$ each have the same respective meanings given in claim 1.

3. A compound according to claim 2 where $R^3$ and $R^4$ are each chlorine and R, $R^1$ and $R^2$ each have the same respective meanings given in claim 2.

4. The compound according to claim 3 where R is ethyl; and $R^1$ and $R^2$ are each hydrogen.

5. A compound according to claim 2 where $R^3$ is —$NR^5$-(lower-alkylene)-$N(R^6)(R^7)$; $R^4$ is —$NR^5$-(lower-alkylene)—$N^+(R^8)$ $(R^9)(R^{10})$ An⁻; and R, $R^1$ and $R^2$ each have the same respective meanings given in claim 2.

6. The compound according to claim 5 where R is ethyl; $R^1$, $R^2$ and $R^5$ are each hydrogen; $R^6$, $R^7$, $R^8$ and $R^9$ are each methyl; $R^{10}$ is benzyl; and lower-alkylene is 1,3-propylene.

7. A compound according to claim 1 having the formula

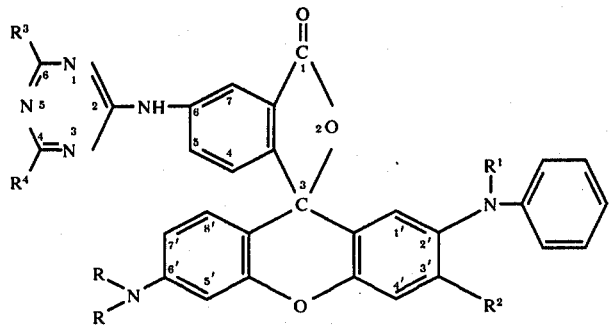

where R, $R^1$, $R^2$, $R^3$ and $R^4$ each have the same respective meanings given in claim 1.

8. A compound according to claim 7 where $R^3$ and $R^4$ are each chlorine and R, $R^1$ and $R^2$ each have the same respective meanings given in claim 7.

9. The compound according to claim 8 where R is ethyl; and $R^1$ and $R^2$ are each hydrogen.

10. A compound according to claim 7 where $R^3$ and $R^4$ are each —$NR^5$-(lower-alkylene)—$N(R^6)(R^7)$; and R, $R^1$ and $R^2$ each have the same respective meanings given in claim 7.

11. The compound according to claim 10 where R is ethyl; $R^1$, $R^2$ and $R^5$ are each hydrogen; $R^6$ and $R^7$ are each methyl; and lower-alkylene is 1,3-propylene.

* * * * *